United States Patent
Olmarker (10) Patent No.: US 10,322,098 B2
(45) Date of Patent: *Jun. 18, 2019

(54) COMPOSITION FOR USE IN THE TREATMENT OF INTERVERTEBRAL DISC-RELATED PAIN

(71) Applicant: STAYBLE THERAPEUTICS AB, Göteborg (SE)

(72) Inventor: Kjell Olmarker, Mölndal (SE)

(73) Assignee: STAYBLE THERAPEUTICS AB (SE)

(*) Notice: Subject to any disclaimer, the term of this patent is extended or adjusted under 35 U.S.C. 154(b) by 0 days.

This patent is subject to a terminal disclaimer.

(21) Appl. No.: 15/995,043

(22) Filed: May 31, 2018

(65) Prior Publication Data
US 2018/0280327 A1 Oct. 4, 2018

Related U.S. Application Data

(63) Continuation of application No. 15/127,560, filed as application No. PCT/EP2015/055991 on Mar. 20, 2015, now abandoned.

(30) Foreign Application Priority Data

Mar. 20, 2014 (SE) ...................................... 1450320

(51) Int. Cl.
| | | |
|---|---|---|
| *A61K 9/00* | (2006.01) | |
| *A61K 9/08* | (2006.01) | |
| *A61K 31/19* | (2006.01) | |
| *A61P 19/00* | (2006.01) | |
| *A61K 9/19* | (2006.01) | |

(52) U.S. Cl.
CPC ............ *A61K 31/19* (2013.01); *A61K 9/0019* (2013.01); *A61K 9/08* (2013.01); *A61P 19/00* (2018.01)

(58) Field of Classification Search
USPC ........................................................ 514/557
See application file for complete search history.

(56) References Cited

U.S. PATENT DOCUMENTS

| 5,385,887 A | 1/1995 | Yim et al. |
| 2007/0253930 A1 | 11/2007 | Roy et al. |
| 2010/0015230 A1 | 1/2010 | Ron |
| 2010/0144631 A1 | 6/2010 | Ron |
| 2012/0022425 A1 | 1/2012 | Yeung et al. |

FOREIGN PATENT DOCUMENTS

| WO | WO 1993/000050 A1 | 1/1993 |
| WO | WO 1997/031661 A1 | 9/1997 |
| WO | WO 2005/046746 A2 | 5/2005 |
| WO | WO 2008/143867 A1 | 11/2008 |

OTHER PUBLICATIONS

Robert D. Helme, et al. "Pain in Older People," Epidemiology of Pain, Jan. 1, 1999, pp. 103-112, XP055195236.
Cheng-Zhen Liang et al: Systematic review/Meta-analysis the relationship between low pH in intervertebral discs and low back pain: a systematic review, Archives of Medical Science, vol. 6, 2012, pp. 952-956, XP055195544.
Keshari K R et al: Lactic acid and proteoglycans as metabolic markers for discogenic back pain, SPINE, vol. 33, No. 3, 2008, pp. 312-317, XP009184667.
Waugh G: "The treatment of chronic degenerative osteoarthritis", Academie Nationale de Medecine. Bulletin vol. 134, No. 5-6, 1950, pp. 103-106, XP009184709.
Maharaj, "Preoperative Intravenous Fluid Therapy Decreases Postoperative Nausea and Pain in High Risk Patient", Ambulatory Anesthesia, 2005; 100, pp. 675-682.
Werthmann "Lactic Acid in daily practice", Sanuvis (lactic acid) as animportant therapy for cell regeneration, 1999, Verlag fi.ir experimentelle Onkologie GmbH • 27316 Hoya• Germany.

*Primary Examiner* — Kathrien A Cruz
(74) *Attorney, Agent, or Firm* — Condo Roccia Koptiw LLP (57) ABSTRACT

The present invention relates to intervertebral disc-related pain, such as low back pain, chronic low back pain, neck pain, chronic neck pain and coccygodynia. A composition for use in the treatment of intervertebral disc-related pain is provided. The composition comprises lactic acid, or a pharmaceutically acceptable salt thereof. The composition is administered into a disc space comprising the nucleus pulposus of an intervertebral disc.

20 Claims, 6 Drawing Sheets figure 1

COMPOSITION FOR USE IN THE TREATMENT OF INTERVERTEBRAL DISC-RELATED PAIN

CROSS REFERENCE TO RELATED APPLICATIONS

This application is a continuation of U.S. patent application Ser. No. 15/127,560, filed Sep. 20, 2016, which is a National Stage Entry under 35 U.S.C. § 371 of Patent Cooperation Treaty Application No. PCT/EP2015/055991, filed Mar. 20, 2015, which claims priority from the Swedish Patent Application No. 1450320-5, filed Mar. 20, 2014, the contents of which are hereby incorporated by reference herein.

TECHNICAL FIELD OF INVENTION

The present invention relates to intervertebral disc-related pain, such as low back pain, chronic low back pain, neck pain, chronic neck pain and coccygodynia, and a composition for use in the treatment of intervertebral disc-related pain.

BACKGROUND

Low back pain, e.g. chronic low back pain, is a common condition that affects about 80% of the adult population during their lifetime. Low back pain is not a specific disease with known pathophysiology, but rather a symptom with many causes. A direct cause, such as a tumor, a fracture, or an infection, has been estimated to be known only in approximately 5-10% of the patients. In the remaining 90-95% of the cases, low back pain is idiopathic, i.e. without known origin.

The structure in the back that seems mainly responsible for low back pain production is the intervertebral disc. An intervertebral disc is arranged between two adjacent vertebrae. The intervertebral disc is typically flexible and allows for motion between the adjacent vertebrae. It is formed by a ring of connective tissue that mainly comprises collagen, and a semi-liquid center comprising e.g. collagen and proteoglycans. The ring is called annulus fibrosus and the center is called nucleus pulposus.

Already at the age of 20-30 years, the intervertebral disc of a human starts to undergo ageing, a process often called disc degeneration. During the ageing process the intervertebral disc may leak or herniate and produce symptoms like low back pain and sciatica. The ageing of the intervertebral disc usually ends at the age of 60-80 years. At this stage, the intervertebral disc has been transformed to solid and dense connective tissue. When this occurs, the intervertebral disc will typically not produce symptoms anymore since it is less likely to leak or herniate. The ageing of the intervertebral disc further implies a reduction in disc height and a reduction of mobility of the spine.

It is known that disc degeneration will induce annular tears that may allow for communication between the center of the intervertebral disc and the outer surface of the annulus fibrosus. Thus, substances, such as inflammatory agents, from the center of the intervertebral disc may leak out onto the outer surface of the annulus fibrosus. Receptors, which are usually silent and arranged on the outer surface of the annulus fibrosus, may then be activated by inflammatory agents typically present in the center of the intervertebral disc during disc degeneration. This mechanism is suggested as one mechanism responsible for low back pain.

Another mechanism that has been suggested to be responsible for low back pain is that there may be newly formed blood vessels and nerves that grow from the outer surface of the annulus fibrosus into the center of the intervertebral disc through the annular tears. It is assumed that these nerves may produce pain when the intervertebral disc moves and exerts pressure on the nerves.

One common procedure for treating low back pain is by surgical stabilization of a vertebral segment comprising an intervertebral disc, which intervertebral disc presumably is producing pain. The rationale is to reduce movements of the pain-producing intervertebral disc in order to avoid the ingrowing nerves to be compressed and produce pain. This surgical treatment is, however, invasive, and not entirely satisfactory.

Another proposed procedure for treating low back pain, or rather sciatica, is by so-called chemonucleolysis, wherein an enzyme is injected into an intervertebral disc in order to dissolve the nucleus pulposus thereby reducing the pressure exerted by the nucleus pulposus of the intervertebral disc on e.g. a nerve.

Further, another proposed procedure for treating low back pain is by rejuvenation, or regeneration, of the intervertebral disc by introduction of e.g. cultivated disc cells and stem cells. However, it seems unlikely that the nutritionally deprived environment in the center of the intervertebral disc would successfully ensure survival of newly introduced cells.

For instance, regeneration promoted by a fibrosing agent has been disclosed in WO 2005/046746. WO 2005/046746 relates e.g. to a method comprising introducing into an intervertebral disc space of a patient in need thereof, a therapeutically effective amount of a fibrosing agent or a composition comprising a fibrosing agent. The fibrosing agent induces a fibrotic response at the intervertebral disc space of the patient, thereby providing the patient with a beneficial result. WO 2005/046746 also relates to an injectable composition comprising a fibrosing agent and a bulking agent.

However, there is still a need in the art to provide a safe and satisfactory procedure to more successfully treat low back pain.

SUMMARY OF THE INVENTION

The object of the present invention is to provide a composition for use in the treatment of intervertebral disc-related pain, such as low back pain, chronic low back pain, neck pain, chronic neck pain and coccygodynia.

The composition for use in the treatment of intervertebral disc-related pain may be formulated such that it may be administered in a therapeutically effective amount by a local injection to an intervertebral disc.

The concept of the present invention is to reduce the intervertebral disc-related pain by accelerating the ageing of an intervertebral disc thereby rendering the intervertebral disc stiffer, e.g. by transformation of the intervertebral disc into solid and dense connective tissue. The transformation of an intervertebral disc into solid and dense connective tissue makes it more stable, and consequently, the intervertebral disc obtains a reduced range of motion. An intervertebral disc transformed into solid and dense connective tissue will neither allow any fluid component to leak out from the disc space, e.g. onto the outer surface of the annulus fibrosus, nor allow nerves to grow into the intervertebral disc.

Already in 1959, Carl Hirsch stated that: "Sooner or later a substance may be found by which a degenerated disc could be transformed to dense connective tissue." in the article "Studies on the Pathology of Low Back Pain" published in The Journal of Bone and Joint Surgery, Vol. 41B, No. 2, p. 237-243, May 1959. Nevertheless, it seems like nobody has until now presented any such substance.

The inventor of the present invention has surprisingly found that the substance successfully could be lactic acid, or a pharmaceutically acceptable salt thereof. This finding is particularly surprising in view of the prior art rather focusing on decreasing the amount of lactic acid, or a pharmaceutically acceptable salt thereof, inside an intervertebral disc causing pain. For instance, US 2012/0022425 A1 discloses a method for reducing lactic acid within an intervertebral disc by injecting a lactic acid inhibitor into the vertebral disc to inhibit production of lactic acid, and thereby alleviating back pain from lactic acid burn. Further, WO 2013/092753 A1 reveals a compound of indole derivatives for inhibiting lactate production in the treatment of for example chronic back pain.

Lactic acid is a carboxylic acid with the chemical formula $CH_3CH(OH)COOH$. As shown in the formula (I) below, lactic acid may in an aqueous solution lose a proton from its carboxyl group, producing the lactate ion $CH_3CH(OH)COO^-$. The mole fraction of lactic acid to lactate ion is 1:1.

$$CH_3CH(OH)COOH(aq) \leftrightarrow CH_3CH(OH)COO^- + H^+ \qquad (I)$$

The lactate ion may together with a counter-ion form a pharmaceutically acceptable salt. The counter-ion may be a metal ion selected from the group consisting of the ions of the following elements: Li, Be, Na, Mg, K, and Ca. Alternatively, the counter-ion may be an organic ion, such as ammonium or choline. Lactic acid, or pharmaceutically acceptable salts thereof, are naturally present in the human body.

The concentration of lactate ion in tissue water of a lumbar intervertebral disc of a patient with back pain has been measured to be within the range of from 1 mmol/L to nearly 12 mmol/L, typically in the range of from 2 mmol/L to 6 mmol/L. These measured values have been presented at page 5 and in FIG. 6 of the scientific article "Oxygen and lactate concentrations measured in vivo in the intervertebral discs of patients with scoliosis and back pain" by Bartels et al., published in Spine 23(1): pp. 1-8, 1998.

As seen in Table 1, the molecular weight of lactate ion is 89.07 g/mol. A molar concentration of 1 mmol lactate ion per liter tissue water in the lumbar intervertebral disc thus corresponds to a mass concentration of 89.07 mg/L. Similarly, a molar concentration of 12 mmol lactate ion per liter tissue water in the disc corresponds to a mass concentration of 1067 mg/L.

In a human, the disc space of a lumbar intervertebral disc has a volume estimated to be approximately from 1.5 mL to 3.0 mL.

In view of the above, the person skilled in the art could easily calculate the amount of lactate, expressed in moles or grams, in the disc. An example is given in Table 1.

TABLE 1

Approximate amounts of lactate ion in a lumbar intervertebral disc of a patient with back pain.

| | |
|---|---|
| Observed lactate ion concentration in the tissue water of a lumbar disc (L3-L4) of a patient with back pain | 1-12 mmol/L |
| Average volume of the disc space of a lumbar disc comprising the tissue water | 1.5-3 mL |

TABLE 1-continued

Approximate amounts of lactate ion in a lumbar intervertebral disc of a patient with back pain.

| | |
|---|---|
| Calculated moles of lactate ion in the tissue water | 0.0015-0.036 mmol |
| Molar weight of lactate ion | 89.07 g/mol |
| Calculated mass of lactate ion in the tissue water | 0.134-3.21 mg |

The lactic acid, the lactate ion or a pharmaceutically acceptable salt thereof may interfere negatively with the function of the cells of the intervertebral disc, in particular the cells that produce the proteoglycans necessary for preventing the disc from ageing.

Ageing of an intervertebral disc is initiated by a reduced supply of nutrients and oxygen via diffusion from the blood vessels in the adjacent vertebrae and from surrounding structures. This will gradually induce an accumulation of metabolic waste products in the intervertebral disc, such as in the nucleus pulposus. One kind of metabolic waste product that may be present is lactic acid, and pharmaceutically acceptable salts thereof.

Lactic acid, and pharmaceutically acceptable salts thereof, may contribute to several mechanisms that will render cellular death in the intervertebral discs, such as intracellular fat accumulation, mitochondrial swelling, chromatin clumping, and liberation of excitotoxic glutamate.

Lactic acid, and pharmaceutically acceptable salts thereof, may liberate $PGE_2$ causing inflammation and production of connective tissue. Further, lactic acid, and pharmaceutically acceptable salts thereof, may stimulate liberation of TGF-beta, which in turn stimulates fibroblasts to produce collagen.

Lactic acid, and pharmaceutically acceptable salts thereof, may also contribute to disseminated intravascular coagulation and consumption coagulopathy, which increases the tendency of red blood cells to aggregate, forming "blood sludge" and makes red blood cells more rigid, in turn, increasing the viscosity of the blood and impairing circulation in the small vessels.

Thus, an increase in the concentration of lactic acid, or pharmaceutically acceptable salts thereof, in an intervertebral disc by administration of a composition comprising lactic acid, or a pharmaceutically acceptable salt thereof, into the disc space of the intervertebral disc would therefore accelerate the ageing of the disc and induce transformation of the nucleus pulposus into connective tissue.

Ageing of the intervertebral disc, including transformation of the nucleus pulposus into connective tissue, renders the intervertebral disc stiffer, and by administering a composition comprising lactic acid, or a pharmaceutically acceptable salt thereof, the ageing may be accelerated in a controllable way. Typically, the concentration of lactic acid, or pharmaceutically acceptable salts thereof, may be increased in an intervertebral disc, more specifically in the disc space, in order to accelerate the ageing.

The inventor has found that a composition comprising lactic acid, or a pharmaceutically acceptable salt thereof, induces a marked transformation of the intervertebral disc, thus making it stiffer. The marked transformation has been interpreted as an accelerated ageing of the intervertebral disc by transformation of the nucleus pulposus to connective tissue. Consequently, the inventor expects improvements for a patient with regard to intervertebral disc-related pain if a composition comprising lactic acid, or a pharmaceutically acceptable salt thereof, is administered into the nucleus pulposus of the intervertebral disc resulting in an increased concentration of lactic acid, or a pharmaceutically acceptable salt thereof, inside the disc space.

The inventor does expect improvements for a patient with regard to intervertebral disc-related pain, such as neck pain, low back pain or coccygodynia, upon administration of lactic acid, or a pharmaceutically acceptable salt thereof, or a composition comprising lactic acid, or a pharmaceutically acceptable salt thereof, into a disc space of an intervertebral disc being, at least partly, responsible for the intervertebral disc-related pain.

According to a first aspect of the invention, a composition for use in the treatment of intervertebral disc-related pain is provided. The composition comprises lactic acid, or a pharmaceutically acceptable salt thereof. The composition is administered into a disc space comprising the nucleus pulposus of an intervertebral disc.

The composition for use in the treatment of intervertebral disc-related pain may comprise at least one of lactic acid and a pharmaceutically acceptable salt thereof. The pharmaceutically acceptable salt is a pharmaceutically acceptable salt comprising a lactate ion and a counter-ion.

Advantages of the composition for use in the treatment of intervertebral disc-related pain according to the present invention is a safer and more efficient treatment of intervertebral disc-related pain, further also being less expensive and less invasive than the treatments, e.g. surgical treatment, known in the state of the art. Further, lactic acid, or pharmaceutically acceptable salts thereof, are biocompatible. The body of a vertebrate, such as a human, is capable of handling, such as degrading, lactic acid, or pharmaceutically acceptable salts thereof, as these compounds are natural compounds, such as waste products, present in the body of the vertebrate.

The inventor suggests that the nucleus pulposus in the disc space of an intervertebral disc may transform to solid and dense connective tissue, similar to the connective tissue of the annulus fibrosus, when a composition for use in the treatment of intervertebral disc-related pain according to the present invention is administered into the nucleus pulposus. For instance, also, blood clotting may take place during the transformation of the nucleus pulposus into connective tissue, rendering the intervertebral disc even more solid and dense. The increased stiffness is expected to result in decreased pain.

According to an embodiment, the composition for use is administered in an amount effective to increase the concentration of lactic acid, or the concentration of lactate ion from the pharmaceutically acceptable salt, in the disc space to above 12 mmol/L.

The composition for use may be administered in an amount effective to increase the concentration of lactic acid or lactate ion in the disc space to a concentration higher than the concentration occurring during natural ageing.

According to an embodiment, the composition for use according to any of claims 1 to 2, wherein the concentration of lactic acid, or the concentration of lactate ion of the pharmaceutically acceptable salt, in the composition is at least 12 mmol/L, for example within the range of from 12 to 12000 mmol/L, such as from 100 to 10000 mmol/L, such as from 500 to 5000 mmol/L, such as from 800 to 2000 mmol/L.

According to an embodiment, the pharmaceutically acceptable salt is a lactate of any of the elements selected from the group consisting of: the alkali metals and the alkaline earth metals. For instance, the pharmaceutically acceptable salt is at least one of lithium lactate, sodium lactate, potassium lactate, beryllium lactate, magnesium lactate and calcium lactate.

According to an embodiment, the pharmaceutically acceptable salt is selected from the group consisting of: ammonium lactate, choline lactate, lithium lactate, sodium lactate, potassium lactate, beryllium lactate, magnesium lactate and calcium lactate.

According to an embodiment, the composition for use is administered to the disc space of an intervertebral disc contributing to the intervertebral disc-related pain.

In an example, the composition for use may be administered to any or all of the intervertebral discs which are suspected to contribute to the intervertebral disc-related pain.

According to an embodiment, lactic acid or a pharmaceutically salt thereof, is administered by local injection into the disc space comprising the nucleus pulposus.

The local injection may typically be performed by a syringe.

According to an embodiment, the lactic acid is administered in a single dosage within the range of from 2 mg to 200 mg, such as from 5 mg to 200 mg, such as from 10 to 100 mg, such as from 10 to 50 mg, such as from 15 to 30 mg. The single dosage corresponds to the amount of lactic acid being administered per disc space.

If a pharmaceutically acceptable salt is administered, the lactate ion of the pharmaceutically salt is administered in an amount corresponding to the single dosage of lactic acid above, taken the molar fraction of lactic acid to lactate ion into account.

According to an embodiment, the composition for use comprising lactic acid, or a pharmaceutically salt thereof, is administered at a single occasion in the single dosage.

According to an embodiment, the composition is in the form of an aqueous solution comprising said lactic acid or a pharmaceutically salt thereof.

Typically, the composition for use in the treatment of intervertebral disc-related pain is provided in a liquid state suitable for local injection.

According to an embodiment, the intervertebral disc-related pain is selected from neck pain, chronic neck pain, low back pain, chronic low back pain, and coccygodynia.

In some examples, the composition may further comprise at least one agent selected from solubilizers, stabilizers, buffers, tonicity modifiers, bulking agents, viscosity enhancers, viscosity reducers, surfactants, cheating agents, preservatives and adjuvants.

In an alternative example, a derivative of lactic acid may additionally or alternatively be administered as a pro-drug, such as ethyl lactate.

In a human, the amount of the composition to be administered may be within the range of from 0.05 mL to 5 mL, such as from 0.1 to 3 mL, e.g. from 0.2 mL to 2 mL. These amounts correspond more or less to the volume of the nucleus pulposus in a human. For a lumbar intervertebral disc, the amount of the composition to be administered may be approximately from 1.5 mL to 3.0 mL. For a cervical intervertebral disc, the amount of the composition to be administered may be approximately 0.5 mL. For a coccygeal intervertebral disc, the amount of the composition to be administered may be approximately 0.2 mL.

By the term "single occasion" is herein meant at a single visit at a medical office, such as during a visit to the doctor e.g. at a hospital. The visit may be no longer than 24 hours, such as from 0.5 to 5 hours. The term typically, but not necessarily, implies that the single dosage is administered by only a single injection at the single occasion. However, the term also covers cases where the single dosage is administered at a single occasion but by several injections, such as from 2 to 10 injections per single occasion, e.g. from 2 to 5 injections per single occasion.

By the term "repeated occasions" is herein meant at more than one visit, i.e. a plurality of visits, at a medical office, such as during more than one visit to the doctor e.g. at a hospital. Each visit may be no longer than 24 hours, such as from 0.5 to 5 hours. The term typically, but not necessarily, implies that the single dosage is administered by only a single injection but at repeated occasions. However, the term also covers cases where the single dosage is administered at repeated occasions but by several injections, such as from 2 to 10 injections per each of said repeated occasions, e.g. from 2 to 5 injections per each of said repeated occasions.

By the term "intervertebral disc" is meant an element lying between two adjacent vertebrae in the spine. Each intervertebral disc forms a cartilaginous joint to allow slight movement of the vertebrae, and acts as a ligament to hold the vertebrae together. An intervertebral disc consists of an outer annulus fibrosus, which surrounds an inner nucleus pulposus. A human vertebral column comprises 23 intervertebral discs: 6 in the neck (cervical region), 12 in the middle back (thoracic region), and 5 in the lower back (lumbar region). In addition, intervertebral discs are also arranged between the coccygeal bones. An intervertebral disc may also be called a disc.

By the term "nucleus pulposus" is meant the jelly-like substance in the middle of an intervertebral disc. The nucleus pulposus comprises chondrocyte-like cells, collagen fibrils, and proteoglycan aggrecans that aggregate through hyaluronic chains. Attached to each aggrecan molecule are the glycosaminoglycan (GAG) chains of chondroitin sulfate and keratan sulfate. The nucleus pulposus acts as a shock absorber, and keeps the two adjacent vertebrae separated.

By the term "annulus fibrosus" is meant, a lamina of fibrous tissue and fibrocartilage formed as at the circumference of the nucleus pulposus. The annular fibrosus serves to distribute pressure evenly across the intervertebral disc.

By the term "disc space" is meant the space of an intervertebral disc which is filled by the nucleus pulposus and which has a circumference defined by the annular fibrosus.

By the term "cranial endplate" is meant the surface of an intervertebral disc facing towards the cranium. The cranial endplate is arranged on opposite side of the intervertebral disc compared to the caudal endplate.

By the term "caudal endplate" is meant the surface of an intervertebral disc facing away from the cranium. The caudal endplate is arranged on opposite side of the intervertebral disc compared to the cranial endplate.

By the term "facet joint" is meant a paired articular structure typically having a joint surface which is covered with articular cartilage. The facet joint is typically enclosed by a capsule. The facet joint form an articulation between the inferior articular process of the vertebrae and the superior articular process of the vertebrae. A facet joint is typically constructed to allow movement and to provide mechanical support to the vertebral column.

By the term "transverese process" is meant a bony formation that extends laterally from the vertebral arch on both sides. It is also termed processus costarius.

By the term "intervertebral disc-related pain" is herein meant a pain related to a pain-producing intervertebral disc. Intervertebral disc-related pain may be pain related to at least one of a cervical vertebra (C), a lumbar vertebra (L), a sacral vertebra (S) and a coccygeal vertebra (Co). Examples of intervertebral disc-related pain may be low back pain, chronic low back pain, neck pain, chronic neck pain and coccygodynia.

By the term "chronic low back pain" is meant low back pain wherein symptoms have occurred during more than 12 weeks.

By the term "chronic neck pain" is meant neck pain wherein symptoms have occurred during more than 12 weeks.

By the term "coccygodynia" is meant pain in the coccyx or tailbone area.

By the term "flexion stiffness" is herein meant a characteristic describing the stiffness of an intervertebral disc arranged in a segment of a vertebral column. The flexion stiffness may be determined by applying a force to the segment of a vertebral column until it reaches a full lateral flexion mode, and by, thereafter, measuring the distance between the transverse processes of the vertebras being arranged on the two opposite sides of the intervertebral disc, respectively. The full lateral flexion mode is defined as the state where the intervertebral disc of the segment of the vertebral column cannot be forced further without breaking of the segment of the vertebral column. This characteristic is measured in millimeter. The flexion stiffness is a way of characterizing the flexural rigidity of the segment of the vertebral column, and more specifically, the flexural rigidity of the intervertebral disc.

Flexural rigidity is generally defined as the force couple required to bend a non-rigid structure to a unit curvature. It is a measure of stiffness of a structural member; the product of modulus of elasticity and moment of inertia divided by the length of the member. In other words, it is the ratio of stress to strain in an elastic material when that material is being bent.

According to a second aspect, there is provided a method for treatment of intervertebral disc-related pain by administration of a therapeutically effective amount of lactic acid, or a pharmaceutically acceptable salt thereof, into the nucleus pulposus of an intervertebral disc of a patient in need thereof. Effects and features of this second aspect of the present invention are analogous to those described above in relation to the first aspect of the present invention.

According to a third aspect, there is provided use of lactic acid, or a pharmaceutically acceptable salt thereof in the manufacture of a medicament for the treatment of intervertebral disc-related pain. Effects and features of this third aspect of the present invention are analogous to those described above in relation to the previous aspects of the present invention.

According to a fourth aspect, there is provided lactic acid, or a pharmaceutically acceptable salt thereof for use in the treatment of intervertebral disc-related pain. Effects and features of this fourth aspect of the present invention are analogous to those described above in relation to the previous aspects of the present invention.

Further features of, and advantages with, the present invention will become apparent when studying the appended claims and the following description. The skilled person realizes that different features of the present invention may be combined to create embodiments other than those described in the following, without departing from the scope of the present invention.

BRIEF DESCRIPTION OF THE DRAWINGS

These and other aspects of the present invention will now be described in more detail, with reference to the appended drawings showing embodiment(s) of the invention.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION OF THE INVENTION

As a vertebrate ages, its intervertebral discs undergo a transformation. An effect of the transformation is that the nucleus pulposus begins to dehydrate and the concentration of proteoglycans in the matrix decreases, resulting is a decreased size of the intervertebral disc. Another effect is that the annulus fibrosus becomes weaker and has an increased risk of tearing. The effects of the transformation of the intervertebral disc may cause intervertebral disc-related pain, e.g. neck pain, low back pain or coccygodynia, in the state before the intervertebral disc gets sufficiently solid and dense.

A vertebral column of a vertebrate comprises vertebrae, which surround and protect a spinal cord. In humans, the vertebral column is situated in the dorsal aspect of torso. Between two adjacent vertebrae, an intermediate intervertebral disc is arranged, i.e. the vertebrae are alternated by intervertebral discs forming the vertebral column. The specific structure and further parts of the vertebral column are known to a person skilled in the art.

Figure 1:
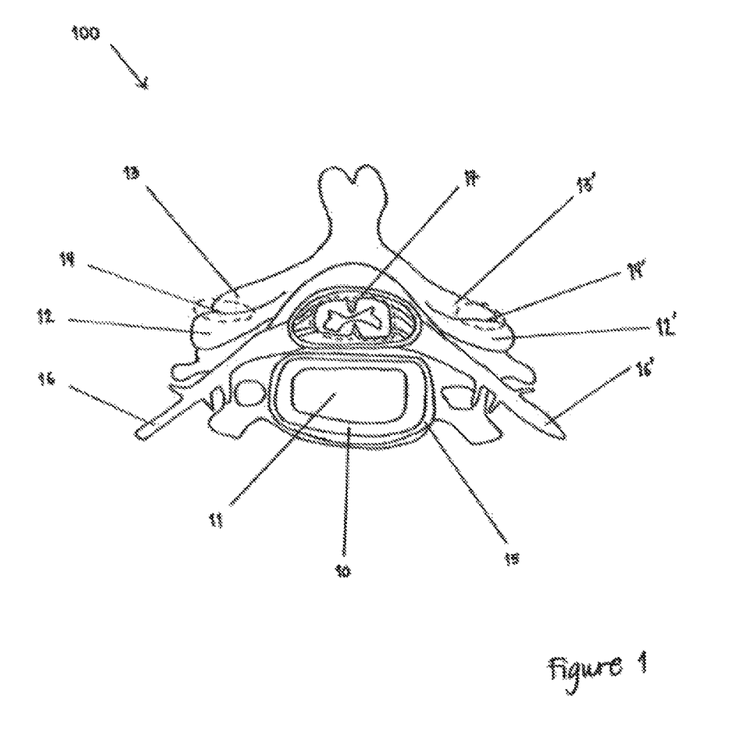
In FIG. 1, a cross section of a vertebral column of a human is schematically shown.

FIG. 1 schematically shows a cross section of a vertebral column 100 of a human. Adjacent to a vertebral body 15 of a vertebra, an intervertebral disc comprising an annulus fibrosus 10 and a nucleus pulposus 11 is arranged. The nucleus pulposus 11 fills up the so-called disc space of the intervertebral disc. The annulus fibrosus 10 surrounds the nucleus pulposus 11 and defines the border of the nucleus pulposus as well as of the disc space.

A spinal cord 17 is situated in the centre of the vertebral column, and adjacent to the intervertebral disc. Spinal nerves 16, 16', extend out from the spinal cord 17 to opposite sides of and closely to the intervertebral disc.

A facet joint 14, 14', is situated between an inferior articular process 13, 13' and a superior articular process 12, 12'. On opposite sides of the spinal cord 17, two facet joints 14, 14', are arranged, respectively. The facet joints 14, 14', are arranged in approximately the same cross-section and plane.

Figure 2:
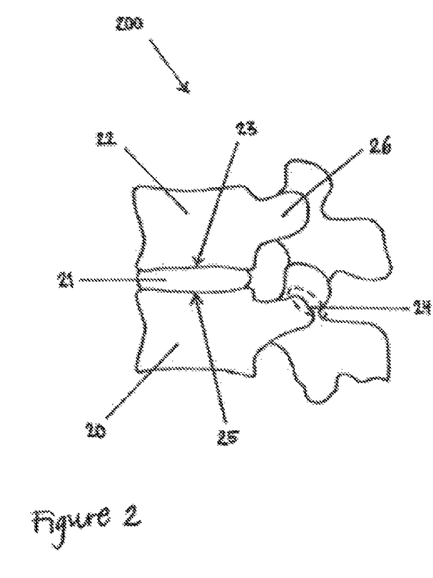
In FIG. 2, two adjacent vertebras of a human vertebral column are schematically shown in a side view.

FIG. 2 schematically shows a segment of a vertebral column 200 comprising two adjacent vertebras 20, 22. A first vertebra 22 and a second vertebra 20 are arranged on opposite sides of an intervertebral disc 21. The first vertebra 22 is arranged relatively closer to the thorax, and the second vertebra 20 is arranged relatively closer to the sacrum. The caudal endplate 23 of the first vertebra 22 and the cranial endplate 25 of the second vertebra 20 are shown in FIG. 2. The cranial endplate 25 and the caudal endplate 23 are facing opposite sides of the intervertebral disc 21.

FIG. 2 also schematically shows how a facet joint 24 is arranged between the inferior articular process of the first vertebra 22 and the superior articular process of the second vertebra 20. A transverese process 26 extends laterally from the vertebral arch.

Figure 3:
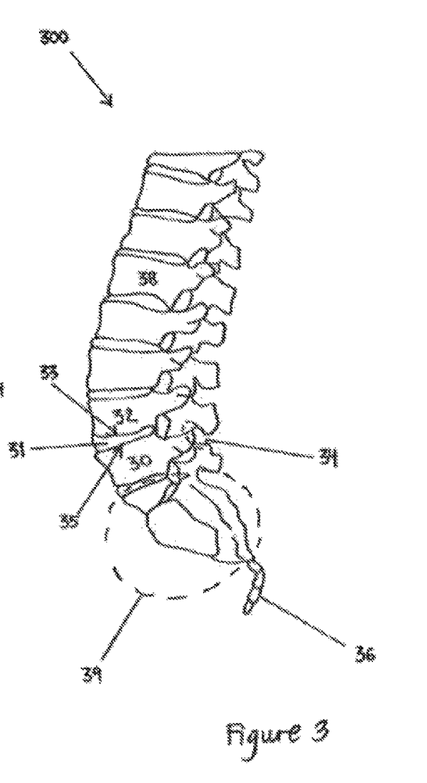
In FIG. 3, a lower part of a vertebral column of a human is schematically shown in a side view.

FIG. 3 schematically shows a lower part of a vertebral column 300. The coccygeal vertebrae 36 of the vertebral column is arranged at an end portion of the lower part of the vertebral column 300. The sacrum 39 of the vertebral column is arranged adjacent to the coccygeal vertebrae 36, closer to the thorax than the coccygeal vertebrae 36. A fifth lumbar vertebra, herein called L5, 30 is arranged adjacent to the sacrum 39, closer to the thorax than the sacrum 39. In a direction from the sacrum 39 towards the thorax, several vertebras are arranged in a row starting with L5, 30. Adjacent to the fifth lumbar vertebra 30, i.e. L5, the following vertebras are arranged in order: a fourth lumbar vertebra 32, i.e. L4, a third lumbar vertebra, i.e. L3, a second lumbar vertebra, i.e. L2, and a first lumbar vertebra 38, i.e. L1; the first lumbar vertebra being arranged relatively closest to the thorax. In between each two adjacent vertebras, an intermediate disc 31 is arranged. Intervertebral discs (not shown) are also imposing the coccygeal vertebrae 36.

EXAMPLES

The procedure for inducing and assessing accelerated transformation of the nucleus pulposus into connective tissue in an intervertebral disc in a pig by administration of a composition for use in the treatment of intervertebral disc-related pain comprising lactic acid, or a pharmaceutically acceptable salt thereof, will herein after be more fully described.

In the present example, a composition for use in treatment of intervertebral disc-related pain comprising lactic acid, or a pharmaceutically acceptable salt thereof, is administered into the nucleus pulposus of an intervertebral disc arranged between the third lumbar vertebra L3 and the fourth lumbar vertebra L4. A person skilled in the art could easily understand that the same procedure may be applied to any intervertebral disc in a vertebral column.

Thus, the steps of the procedure are the following:

100. preparing a composition comprising lactic acid, or a pharmaceutically acceptable salt thereof;

101. anaesthetizing a pig comprising a vertebral column comprising the intervertebral disc comprising the nucleus pulposus into which the composition is to be administered;

102. allow access to the intervertebral disc through a lateral incision between the lowest rib and the iliac crest of the pig;

103. incising the intervertebral disc;

104. administering, herein by locally injecting, the composition into the nucleus pulposus by an injection needle;

105. allowing the pig to move freely for seven days after recovering from anaesthesia;

106. harvesting the lumbar spine en bloc, the harvested segment comprising the vertebral bodies and the intervertebral disc comprising the nucleus pulposus subjected to injection, but without the posterior elements (the vertebral arch and facet joints);

107. measuring the distance between the transverse processes at the levels of discs L 2-3, L 3-4, L4-5 without any external force applied;

108. applying an external force to the segment of the vertebral column until a full lateral flexion mode is achieved for the lumbar spine specimen;

109. measuring the distance between the transverse processes at the levels of discs L 2-3, L 3-4, L4-5 under full lateral flexion;

110. performing a cross-section of the discs and measuring the length (anterio-posterior direction) and the width (bilateral direction) of the disc space.

Example 1: Preparation of a Composition Comprising Lactic Acid

A pure solution of lactic acid was purchased from Sigma Aldrich (product number: 69775 Fluka; CAS number: 50-21-5, Stockholm, Sweden). As shown in Table 2, the molecular weight of lactic acid is 90.08 g/mol and the density of the pure solution from Sigma Aldrich was 1.209 g/mL, respectively.

The concentration of lactic acid in the pure solution from Sigma Aldrich was consequently calculated to be 0.0134 mol/mL, equals 13.4 mol/L.

The pure solution of lactic acid was thereafter diluted 10 times using distilled water at room temperature. More explicitly, 1 mL of the pure solution of lactic acid from Sigma Aldrich was diluted with 9 mL of distilled water. The resulting concentration of lactic acid in the prepared composition was consequently 1.34 mol/L.

TABLE 2

Amounts of lactic acid in the prepared composition.

| | |
|---|---|
| Density of lactic acid in the pure lactic acid solution | 1.209 g/mL |
| Molar weight of lactic acid | 90.08 g/mol |
| Calculated concentration of lactic acid in the pure lactic acid solution | 13.4 mol/L |
| Degree of dilution | 10% |
| Calculated concentration of lactic acid in the diluted pure lactic acid solution | 1.34 mol/L |

Example 2: Administration of a Composition Comprising Lactic Acid to the Nucleus Pulposus of an Intervertebral Disc in a Pig by Local Injection Two pigs were anesthetized and placed on their right side. Access to the L4-5 intervertebral disc was obtained through a lateral incision between the lowest rib and the iliac crest on the left side of each pig. Thereafter, the L3-4 intervertebral disc was incised with a scalpel.

The composition comprising lactic acid was injected by a syringe into the nucleus pulposus of the L3-4 intervertebral disc. The composition comprising lactic acid in a total concentration of 1.34 mol/L was injected in an amount of approximately 0.2 mL into the nucleus pulposus, as shown in Table 3. The composition was injected in a single step at a single occasion.

Both pigs seemed to tolerate the procedure well and no adverse reaction such as decreased mobility or vocalization was observed during the period of seven days until harvest. At harvest, the pigs were killed.

TABLE 3

Amount of lactic acid in the composition administered to a L3-4 interverebral disc of a pig.

| | |
|---|---|
| Volume of injected diluted pure lactic acid solution | 0.2 mL |
| Calculated moles of lactic acid in the injection | 0.268 mmol |
| Calculated mass of lactic acid in the injection | 23.9 mg |

Example 3: Assessment of Transformation of Nucleus Pulposus into Connective Tissue in an Intervertebral Disc Administered with a Composition Comprising Lactic Acid The injection site was observed by the naked eye. No adverse reaction at the injection site, such as bleedings, inflammation or necrosis, was observed in any of the pigs. The segment of the vertebral column extending from the lumbar vertebra L2 to the sacral vertebra S1 was removed. The facet joints were removed, thus allowing full flexibility of the discs with no restraints from other structures.

Figure 4:
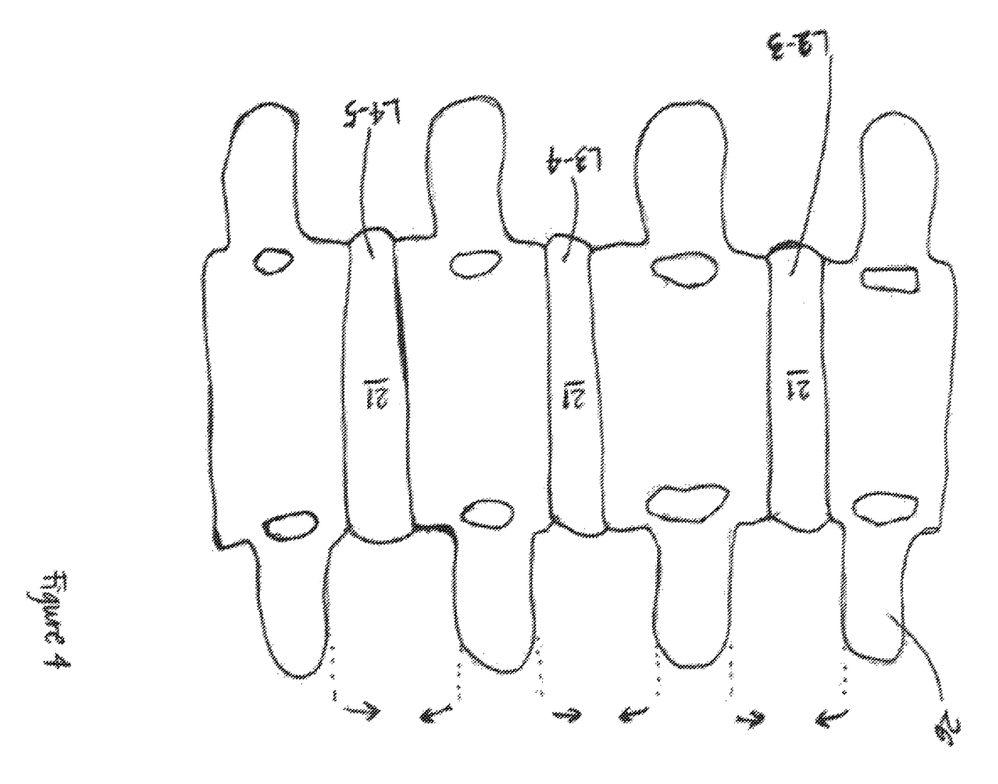
In FIG. 4, a vertebral segment is schematically shown in a posterior view.

3a—Flexion Stiffness of the Intervertebral Disc before and after Administration of the Composition, Respectively In FIG. 4, a segment of a vertebral column comprising intervertebral discs 21, namely the intervertebral discs L2-3, L3-4 and L4-5, is shown.

During the assessment of flexion stiffness, the distance between each of the respective adjacent transverse processes 26 of the vertebral column, thus, the segment of the vertebral column extending from the lumbar vertebra L2 to the sacral vertebra S1, was measured by calipers when the segment of the vertebral column was arranged in a mode without any external load applied.

Thereafter, the vertebral column, thus, the segment of the vertebral column extending from the lumbar vertebra L2 to the sacral vertebra S1, was manually forced into a full lateral flexion mode by applying an external force to each of the two end portions of the part of the vertebral column until a critical limit was met, i.e. until the full flexion mode was achieved. The motion of the transverse processes upon an applied force is schematically shown in FIG. 4 by arrows with dotted lines.

The critical limit was defined as the point just before the breaking point of the segment of the vertebral column. Thus, the external force was applied such that a maximum lateral flexion was obtained without breaking any part of the vertebral segment.

The force was assumed to be similar for the segment of the vertebral column in each of the both pigs. In the position of full lateral flexion, the distance between the adjacent transverse processes for the discs L 2-3, L 3-4, L4-5 were measured by calipers.

The distance between the adjacent transverse processes for a certain disc in the mode without external load was subtracted from the distance between the same transverse processes in the mode with an external load applied to achieve full lateral flexion mode, thereby providing a value of the balanced distance obtained by the full lateral flexion. The balanced value for the injected intervertebral disc reflects the flexion stiffness of the intervertebral disc being treated with a composition for use in the treatment of intervertebral disc-related pain compared to a non-injected intervertebral disc.

The flexion stiffness is an indirect measure of the transformation of the nucleus pulposus into connective tissue, as the smaller the balanced value, the stiffer the intervertebral disc. The stiffer the intervertebral disc, the higher the content of solid and dense connective tissue. Hence, the flexion stiffness indicates whether the nucleus pulposus has undergone a transformation into connective tissue, i.e. an accelerated ageing, or not.

The measurements show that the injected discs (L 3-4) had a much smaller balanced value than the non-injected adjacent discs (L 2-3; L 4-5), which indicates a higher flexion stiffness of the injected disc. Thus, an accelerated transformation of the nucleus pulposus into connective tissue had taken place inside the disc space of the injected disc compared to inside the disc spaces of the non-injected discs (see Table 4).

TABLE 4

Difference in distance between transverse processes before and upon full lateral flexion (mm ± SD).

| Intervertebral disc | Distance (mm) |
|---|---|
| L 2-3 | 3.1 ± 1.1 |
| L 3-4 | 0.3 ± 0.6 |
| L 4-5 | 2.7 ± 0.9 |

3b—Dimension of the Disc Space Before and after Administration of the Composition, Respectively The intervertebral discs (L2-3, L3-4, L4-5) were cross-sectioned and the length of the disc space (anterio-posterior direction) and the width (bilateral direction) of the disc space were measured by calipers.

Figure 5:
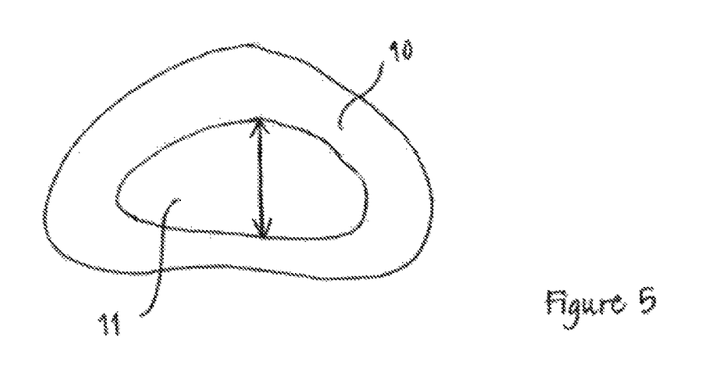
In FIG. 5, it is schematically shown how the anterioposterior length of a cross-section of an intervertebral disc is measured.
Figure 6:
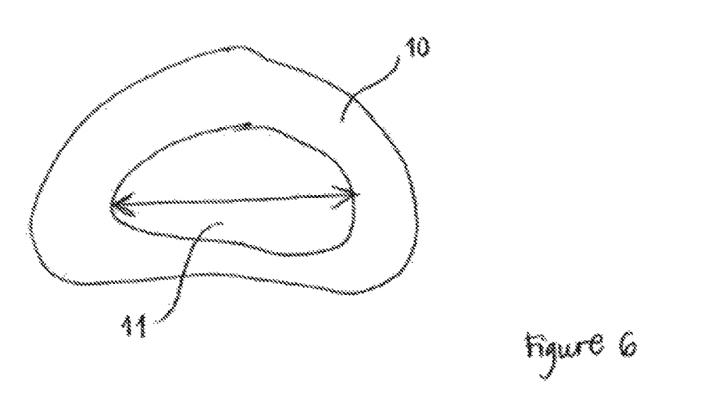
In FIG. 6, it is schematically shown how the bilateral width of a cross-section of an intervertebral disc is measured.

In FIGS. 5 and 6, an intervertebral disc is schematically shown in cross-section. The intervertebral disc comprises the annulus fibrosus 10, and a disc space defined by the annulus fibrosus and comprising the nucleus pulposus 11.

In FIG. 5, an arrow schematically shows how the anterio-posterior length of the disc space of the intervertebral disc is measured. In FIG. 6, an arrow schematically shows how the bilateral width of the disc space of the intervertebral disc is measured.

As seen from the measurements, the average anterio-posterior length of the disc space was significantly lower in the injected discs (L 3-4) than in the adjacent non-injected discs (L2-3, L4-5) (see Table 5).

TABLE 5

Average antero-posterior length of the disc space (mm ± SD).

| Intervertebral disc | Length (mm) |
|---|---|
| L 2-3 | 22.0 ± 1.0 |
| L 3-4 | 13.5 ± 1.3 |
| L 4-5 | 21.3 ± 2.2 |

As seen from the measurements, the average bilateral width of the disc space was significantly lower in the injected discs (L 3-4) than in the adjacent non-injected discs (L2-3, L4-5) (see Table 6).

TABLE 6

Average bilateral width of the disc space (mm ± SD).

| Intervertebral disc | Width (mm) |
|---|---|
| L 2-3 | 8.4 ± 0.7 |
| L 3-4 | 4.0 ± 1.4 |
| L 4-5 | 8.6 ± 2.3 |

Figure 7:
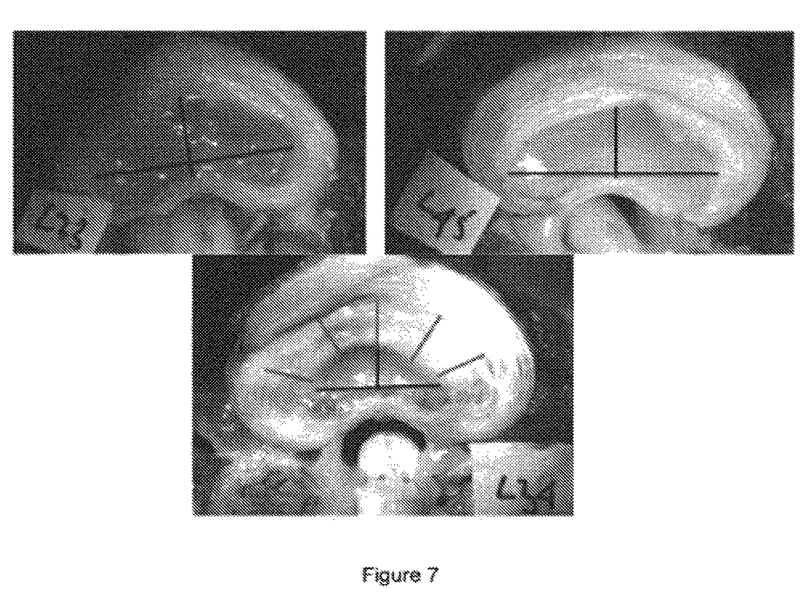
FIG. 7 shows three intervertebral discs in cross-section, and the transformation of the nucleus pulposus into connective tissue in the disc administered with a composition according to an embodiment of the present invention.

FIG. 7 shows the intervertebral discs L2-3, L-3-4 and L4-5, respectively, from one of the pigs in the experiments above. Width and depth of the disc space are indicate by bold straight lines corresponding to the schematic drawings in FIGS. 5-6.

In FIG. 7, it is further shown how the disc space of the injected L3-4 disc had a much smaller cross-sectional area than the non-injected L2-3 and L4-5 discs, respectively. Thus, it can be verified by the naked eye that there was newly formed connective tissue in the disc space former comprising nucleus pulposus in the injected intervertebral discs.

Conclusion of the Experiments

It is evident that the disc space in the two non-injected discs (L2-3) and (L4-5) is much deeper and wider than the disc (L3-4) which had been administered with the composition comprising lactic acid. It seems that the former disc space has been exchanged with newly formed connective tissue (emphasized by the fading, additional lines in an arc-like arrangement, in FIG. 7), such that the annular fibrosus (formed by a ring of connective tissue that mainly comprises collagen) has expended at the expense of the nucleus pulposus that has decreased in size.

Thus, a flexion stiffness of the injected intervertebral discs is achieved, and the stiffness can suppress the pain experienced by a patient having intervertebral disc-related pain. An advantage of this way of treatment of intervertebral disc-related pain, is that the treatment is less invasive than current treatment methods, such as compared to the current treatment method of arthrodesis.

In the examples described above, the intervertebral disc was arranged in the lumbar spine. However, a similar process is expected to be observed in an intervertebral disc arranged in the cervical spine or in the coccygeal spine.

To observe the effects of lactic acid on a cell level, studies were conducted on fibroblasts, commonly present in connective tissue such as the annulus fibrosus, and nucleus pulposus cells, commonly present in the nucleus pulposus, respectively. As a measure on how the cells transformed in response to treatment of lactic acid, the collagen production in the cells was studied.

Study of Collagen Production in Fibroblasts Upon Treatment with Lactic Acid

Culture of Adult Human Dermal Fibroblasts (HDFa)

Human dermal fibroblasts isolated from adult skin, so-called HDFa, (Life Technologies Frederick, USA) were cultured and studied. Mature human intervertebral disc cells have been described as being fibrocytic (or fibroblast-like) in the outer annulus fibrosus. Fibroblasts are the most common type of cell found in connective tissue. Fibroblasts may naturally secrete collagen proteins that are used to maintain a structural framework for many tissues and also play an important role in wound healing.

Firstly, cryopreserved fibroblasts were thawed in a 37° C. water bath. The thawed fibroblasts were then dispersed by using a 1 milliliter pipette to move the suspension of thawed fibroblasts up and down in the vial. The dispersed fibroblasts were then diluted in trypan blue solution (Cat. No. 15250-

061, Lot No. 1311086, Gibco Life Technologies), and the concentration of viable fibroblast was determined by a hemacytometer.

The dispersed fibroblasts were then diluted again, this time in supplemented Medium 106 to a concentration of $2.5 \times 10^4$ viable fibroblasts per milliliter. 5 ml of fibroblast suspension was then added to a T25 cell culture flask having a volume of 25 cm$^3$ to achieve an initial density of $5.0 \times 10^3$ viable fibroblasts per milliliter in the T25 flask by further dilution with supplemented Medium 106.

The supplemented Medium 106 consisted of Medium 106 (Cat. No. M-106-500, Life Technologies, Paisley, Great Britain) supplemented with Low Serum Growth Supplement, LSGS, (Life Technologies, Paisley, Great Britain) at a concentration of fetal bovine serum of 2% by volume The T25 flask comprising the prepared fibroblasts was swirled to distribute the fibroblasts in the medium. The cell culture was thereafter incubated in a 37° C., 5% $CO_2$/95% air humidified cell culture incubator for 72 hours.

At confluence, the fibroblasts were diluted in the supplemented media to avoid alternations in cell phenotype.

Preparation of Lactic Acid

Lactic acid (Fluka 69775, Sigma-Aldrich, Stockholm, Sweden) was weighted into a sterile 10 mL tube or 50 mL tube. Milli-Q water (>18.2Ω) was added to prepare a stock solution of lactic acid. The stock solution was mixed and stored before preparing final solutions of lactic acid with varying concentrations. The period of storage was less than 1 hour at ambient temperature, or, alternatively, less than 24 hours at a temperature of 4° C.

Effect of Lactic Acid on Collagen Production in Adult Human Dermal Fibroblasts (HDFa)

Fibroblasts cultured as described above were detached from the cell culture flask and placed on 6-well plates at an initial density of $6.0 \times 10^4$ viable cells per well. The fibroblasts were grown in supplemented Medium 106. The fibroblasts in some of the wells were also treated with lactic acid (Fluka 69775, Sigma-Aldrich, Stockholm, Sweden) in various concentrations: 0, 0.5, 2, 5, 10, 20 and 50 mg/mL, respectively. The fibroblasts were incubated in a 37° C., 5% $CO_2$/95% air humidified cell culture incubator for 48 hours.

To study the effect of lactic acid on the collagen production in the fibroblasts, a spectrophotometric method called Soluble Collagen Assay (QuickZyme Biosciences, Leiden, Netherlands) based on binding of Sirius Red dye to collagen, was applied. The study was performed twice.

Cell media was collected from each well and 140 μL was pipetted into a 96-well plate. Samples were taken in duplicates. Medium samples were mixed thoroughly with 60 μL Sirius Red dye solution by pipetting up and down at least five times. The 96-well plate was centrifuged at 3000×g for 1 hour. All of these steps were performed at a temperature below 25° C., for example the centrifugation was performed at 4° C.

The centrifuged sample was washed and the supernatant removed. The cell pellet was resuspended in 150 μL detection solution by thoroughly mixing by pipetting up and down at least ten times. Thereafter, 100 μL of each sample was transferred into a new 96-well plate and collagen content was measured spectrophotometrically at an optical density of 540 nm.

Figure 8:
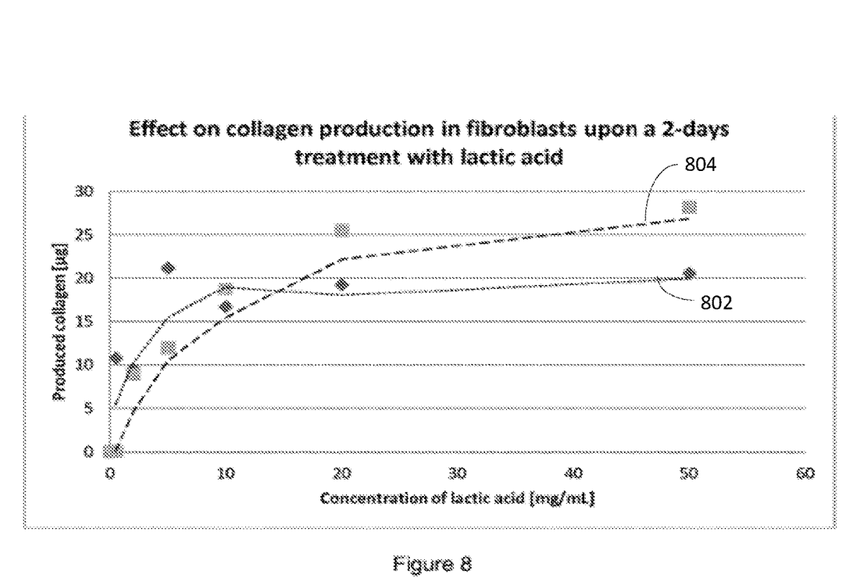
FIG. 8 shows the experimental results from the study of collagen production in fibroblasts upon treatment with lactic acid.

From the two studies each performed in duplicates, it was clearly shown that addition of lactic acid to fibroblasts increases the average production of collagen in the fibroblasts, as indicated in Table 7 and FIG. 8. The average production was measured after 2 days of treatment with lactic acid.

In FIG. 8, the results from the first set of the study are presented by diamonds, while the results from the second set of the study are presented by squares. A two-period moving average trendline has been included to schematically show the trend in collagen production for each set. The trendline for the first set is presented by a dotted line and is labeled 802, and the trendline for the second set is presented by a dashed line and is labeled 804. The x-axis shows the concentration of the lactic acid added to the wells comprising fibroblasts, and the y-axis shows the average amount of produced collagen in these wells upon measurement after two days from addition of the lactic acid into the wells.

More particular, the increase in production of collagen was significant when lactic acid was added to a concentration of at least 2 mg/mL, such as at least 5 mg/mL, in the well. Further, it was shown that the collagen production increased with increasing lactic acid concentration up to at least 20 mg/mL or at least 50 mg/mL as also indicated in FIG. 8.

TABLE 7

Effect on collagen production in fibroblasts of lactic acid.

| Concentration of lactic acid [mg/mL] | 1$^{st}$ set of study: Average amount of produced collagen per well [μg] | Standard deviation in the 1$^{st}$ set of study | 2$^{nd}$ set of study: Average amount of produced collagen per well [μg] | Standard deviation in the 2$^{nd}$ set of study |
|---|---|---|---|---|
| 0 | 0.033 | 0.1 | 0.0711 | 0.111 |
| 0.5 | 10.8 | 12 | 0.0995 | 0.0435 |
| 2 | 9.57 | 4 | 8.94 | 5.72 |
| 5 | 21.2 | 0.8 | 12.0 | 0.281 |
| 10 | 16.7 | 1 | 18.8 | 4.46 |
| 20 | 19.3 | 1.5 | 25.5 | 2.15 |
| 50 | 20.6 | 1 | 28.2 | 0.24 |

As the average collagen production is correlated to the number of cells able to produce collagen, the slight difference in average collagen production between the first set and the second set of the study may be due to a natural variance in the number of cells in the studied wells.

Study of Collagen Production in Nucleus Pulposus Cells Upon Treatment with Lactic Acid Culture of Human Nucleus Pulposus Cells Nucleus pulposus (NP) cells isolated from humans (4800, ScienCell, USA) were cultured and studied. NP cells are intervertebral disc cells in the nucleus pulposus.

Firstly, cryopreserved NP cells were thawed in a 37° C. water bath. The thawed NP cells were then suspended in supplemented Nucleus Pulposus Cell Medium, and thereafter seeded in a T75 cell culture flask having a volume of 75 cm$^3$ and being coated on its inside with poly-L-lysine (0413, ScienCell, USA). The initial seeding density was $5.0 \times 10^3$ viable NP cells per milliliter.

The supplemented Nucleus Pulposus Cell Medium consisted of Nucleus Pulposus Cell Medium (4801, ScienCell, USA) supplemented with 2% by volume of fetal bovine serum (0010, ScienCell, USA), 1× Nucleus Pulposus Cell Growth Supplement (4852, ScienCell, USA) and 1× penicillin/streptomycin solution (0503, ScienCell, USA).

The T75 flask comprising the prepared NP cells was swirled to distribute the NP cells in the medium. The cell culture was thereafter incubated in a 37° C., 5% $CO_2$/95% air humidified cell culture incubator over night.

At confluence, the fibroblasts were diluted in the supplemented media to avoid alternations in cell phenotype, cell proliferation and/or cell differentiation.

Preparation of Lactic Acid

Lactic acid (PURAC PF 90, Batch No. 1406001940, Corbion Purac, the Netherlands) was weighted into a sterile 10 mL tube or 50 mL tube. Milli-Q water (>18.2Ω) was added to prepare a stock solution of lactic acid. The stock solution was mixed and stored before preparing final solutions of lactic acid with varying concentrations. The period of storage was less than 1 hour at ambient temperature, or, alternatively, less than 24 hours at a temperature of 4° C.

Effect of Lactic Acid on Collagen Production in Human Nucleus Pulposus Cells

NP cells cultured as described above were detached from the cell culture flask and placed on 6-well plates at an initial density of $4.5 \times 10^4$ viable cells per well. The NP cells were grown in supplemented Nucleus Pulposus Cell Medium. The NP cells in some of the wells were also treated with lactic acid (PURAC PF 90, Batch No. 1406001940, Corbion Purac, the Netherlands) in various concentrations: 0, 0.5, 5, 10, 20 and 50 mg/mL, respectively. The NP cells were incubated in a 37° C., 5% $CO_2$/95% air humidified cell culture incubator for 48 hours.

To study the effect of lactic acid on the collagen production in the NP cells, a spectrophotometric method called Soluble Collagen Assay (QuickZyme Biosciences, Leiden, the Netherlands) based on binding of Sirius Red dye to collagen, was applied.

Cell media was collected from each well and 140 μL was pipetted into a 96-well plate. Samples were taken in triplicates. Medium samples were mixed thoroughly with 60 μL Sirius Red dye solution by pipetting up and down at least five times. The 96-well plate was centrifuged at 1500×g for 2 hours. All of these steps were performed at a temperature below 25° C., for example the centrifugation was performed at 4° C.

The centrifuged sample was washed and the supernatant removed. The cell pellet was resuspended in 150 μL detection solution by thoroughly mixing by pipetting up and down at least ten times. Thereafter, 100 μL of each sample was transferred into a new 96-well plate and collagen content was measured spectrophotometrically at an optical density of 540 nm.

In order to suit the apparatus of measurement, the cells were diluted in phosphate buffer solution (PBS) at a ratio of 1:1.

Figure 9:
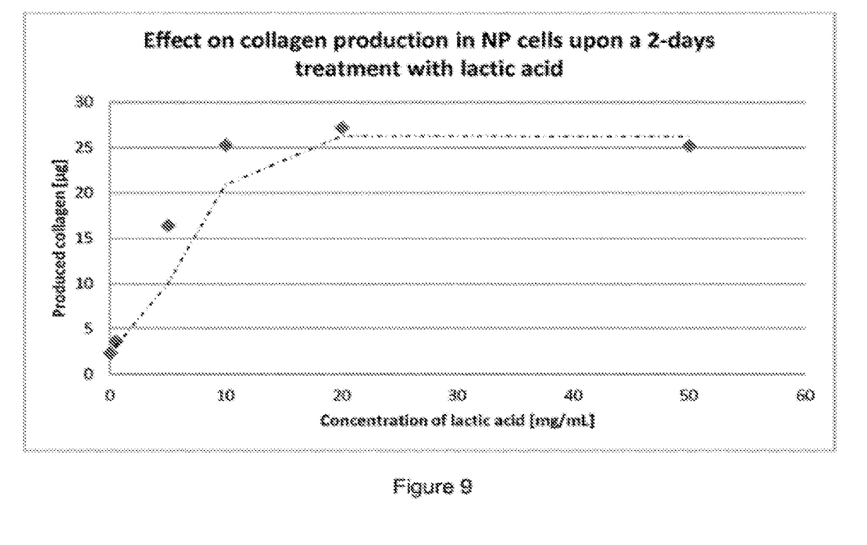
FIG. 9 shows the experimental results from the study of collagen production in nucleus pulposus cells upon treatment with lactic acid.

From the study performed in triplicate, it was clearly shown that addition of lactic acid to NP cells increases the average production of collagen in the NP cells, as indicated in Table 8 and FIG. 9. The average production was measured after 2 days of treatment with lactic acid.

In FIG. 9, the results from the study are presented by diamonds. A two-period moving average trendline has been included to schematically show the trend in collagen production. The x-axis shows the concentration of the lactic acid added to the wells comprising NP cells, and the y-axis shows the average amount of produced collagen in these wells upon measurement after two days from addition of the lactic acid into the wells.

More particular, the increase in production of collagen was significant when lactic acid was added to a concentration of at least 5 mg/mL in the well. Further, it was shown that the collagen production increased with increasing lactic acid concentration up to about 10-20 mg/mL, where a plateau was reached as also indicated in FIG. 9. The decrease in collagen production at 50 mg/mL is interpreted such that a treatment with lactic acid in such a high concentration may have cytotoxic effects causing cell death.

TABLE 8

Effect on collagen production in NP cells of lactic acid

| Concentration of lactic acid [mg/mL] | Average amount of produced collagen per well [μg] | Standard deviation |
|---|---|---|
| 0 | 2.33 | 0.267 |
| 0.5 | 3.58 | 1.48 |
| 5 | 16.4 | 0.339 |
| 10 | 25.3 | 1.11 |
| 20 | 27.2 | 0.513 |
| 50 | 25.2 | 2.82 |

CONCLUSION

The inventors believe that the use according to embodiments of the present invention will treat intervertebral disc-related pain also in humans.

The expected transformation into connective tissue of the intervertebral disc subjected to injection of a substance, such as a lactic acid, or a pharmaceutically acceptable salt thereof, may be observed in vivo. Typically, the procedure will be conducted under anaesthesia or light sedation, and by using radiologic guidance. Thus, the treatment procedure will be similar to a radiologic assessment of the intervertebral disc, a so called discography, when a contrast medium is injected into the intervertebral disc under radiologic guidance.

Other substances capable of inducing accelerated degeneration of an intervertebral disc may also be considered as substitutes and/or alternatives to lactic acid or a pharmaceutically acceptable salt thereof.

The invention claimed is:

1. A method for treating intervertebral disc-related pain, the method comprising administering a composition into a disc space comprising the nucleus pulposus of an intervertebral disc, wherein said composition comprises lactic acid, or a pharmaceutically acceptable salt thereof.

2. The method according to claim 1, wherein the composition is administered in an amount effective to increase the concentration of lactic acid, or the concentration of lactate ion from the pharmaceutically acceptable salt, in said disc space to above 12 mmol/L.

3. The method according to claim 1, wherein the concentration of lactic acid, or the concentration of lactate ion of the pharmaceutically acceptable salt, in the composition is at least 12 mmol/L.

4. The method according to claim 1, wherein the pharmaceutically acceptable salt is a lactate of any of the elements selected from the group consisting of: the alkali metals and the alkaline earth metals.

5. The method according to claim 1, wherein the pharmaceutically acceptable salt is selected from the group consisting of: ammonium lactate, choline lactate, lithium lactate, sodium lactate, potassium lactate, beryllium lactate, magnesium lactate and calcium lactate.

6. The method according to claim 1, wherein said composition is administered to the disc space of an intervertebral disc contributing to the intervertebral disc-related pain.

7. The method according to claim 1, wherein said lactic acid or a pharmaceutically salt thereof, is administered by local injection into the disc space comprising the nucleus pulposus.

8. The method according to claim 1, wherein the lactic acid is administered in a single dosage within the range of from 2 mg to 200 mg.

9. The method according to claim 1, wherein the lactic acid is administered in a single dosage within the range of from 5 mg to 200 mg.

10. The method according to claim 8, wherein said lactic acid or a pharmaceutically salt thereof, is administered at a single occasion in said single dosage.

11. The method according to claim 1, wherein said composition is in the form of an aqueous solution comprising said lactic acid or a pharmaceutically salt thereof.

12. The method according to claim 1, wherein said intervertebral disc-related pain is selected from neck pain, chronic neck pain, low back pain, and chronic low back pain.

13. The method according to claim 1, wherein said intervertebral disc-related pain is coccygodynia.

14. The method according to claim 3, wherein the concentration of lactic acid, or the concentration of lactate ion of the pharmaceutically acceptable salt, in the composition is within the range of 12 to 12000 mmol/L.

15. The method according to claim 3, wherein the concentration of lactic acid, or the concentration of lactate ion of the pharmaceutically acceptable salt, in the composition is within the range of 100 to 10000 mmol/L.

16. The method according to claim 3, wherein the concentration of lactic acid, or the concentration of lactate ion of the pharmaceutically acceptable salt, in the composition is within the range of 500 to 5000 mmol/L.

17. The method according to claim 3, wherein the concentration of lactic acid, or the concentration of lactate ion of the pharmaceutically acceptable salt, in the composition is within the range of 800 to 2000 mmol/L.

18. The method according to claim 9, wherein the lactic acid is administered in a single dosage within the range of 10 to 100 mg.

19. The method according to claim 9, wherein the lactic acid is administered in a single dosage within the range of such as from 10 to 50 mg.

20. The method according to claim 9, wherein the lactic acid is administered in a single dosage within the range of 15 to 30 mg.

* * * * *